US008718289B2

(12) United States Patent
Shridhar et al.

(10) Patent No.: US 8,718,289 B2
(45) Date of Patent: May 6, 2014

(54) SYSTEM FOR ACTIVE NOISE CONTROL WITH PARALLEL ADAPTIVE FILTER CONFIGURATION

(75) Inventors: Vasant Shridhar, Royal Oak, MI (US); Duane Wertz, Byron, MI (US)

(73) Assignee: Harman International Industries, Incorporated, Northridge, CA (US)

( * ) Notice: Subject to any disclaimer, the term of this patent is extended or adjusted under 35 U.S.C. 154(b) by 803 days.

(21) Appl. No.: 12/352,435

(22) Filed: Jan. 12, 2009

(65) Prior Publication Data

US 2010/0177905 A1 Jul. 15, 2010

(51) Int. Cl.
*A61F 11/06* (2006.01)
*G10K 11/16* (2006.01)
*H03B 29/00* (2006.01)

(52) U.S. Cl.
USPC ..................... 381/71.1; 381/71.11; 381/71.12

(58) Field of Classification Search
CPC ............ G10K 11/1784; G10K 11/178; G10K 11/1786; G10K 11/1788; G10K 2210/30232; G10K 2210/3045; G10K 2210/3023; G10K 2210/3046; G10K 2210/3042; G10K 2210/1282; G10K 2210/128; G10K 2210/1082; G10K 2210/00; H04R 2410/05
USPC ............ 381/71.11, 71.12, 71.13, 71.14, 71.9, 381/71.8, 71.1, 71.7
See application file for complete search history.

(56) References Cited

U.S. PATENT DOCUMENTS

| | | | | |
|---|---|---|---|---|
| 4,589,137 | A | 5/1986 | Miller | 381/94 |
| 4,628,156 | A | 12/1986 | Irvin | 379/410 |
| 4,654,871 | A | 3/1987 | Chaplin et al. | 381/71 |
| 4,677,678 | A | 6/1987 | McCutchen | 381/72 |
| 4,736,431 | A | 4/1988 | Allie et al. | |
| 4,910,799 | A | 3/1990 | Takayama | 455/296 |
| 4,941,187 | A | 7/1990 | Slater | 381/86 |
| 4,947,356 | A | 8/1990 | Elliott et al. | |
| 4,953,217 | A | 8/1990 | Twiney et al. | 381/72 |
| 4,977,600 | A | 12/1990 | Ziegler | 381/71 |
| 4,985,925 | A | 1/1991 | Langberg et al. | 381/72 |
| 4,998,241 | A | 3/1991 | Brox et al. | 370/32.1 |
| 5,001,763 | A | 3/1991 | Moseley | 381/71 |
| 5,033,082 | A | 7/1991 | Eriksson et al. | 379/410 |
| 5,081,682 | A | 1/1992 | Kato et al. | 381/57 |

(Continued)

FOREIGN PATENT DOCUMENTS

| | | | |
|---|---|---|---|
| CN | 1688179 A | 10/2005 | H04R 3/00 |
| EP | 0 622 779 A2 | 11/1994 | |

(Continued)

OTHER PUBLICATIONS

Extended European Search Report from European Application No. EP 10150426.4-2213, dated May 26, 2010, 7 pgs.

(Continued)

*Primary Examiner* — Vivian Chin
*Assistant Examiner* — Con P Tran
(74) *Attorney, Agent, or Firm* — Brooks Kushman P.C.

(57) ABSTRACT

An active noise control system includes a plurality of adaptive filters. The plurality of adaptive filters each receives an input signal representative of an undesired sound. The adaptive filters may each generate an output signal based on the input signal. The output signals are used to generate an anti-noise signal configured to drive a speaker to produce sound waves to destructively interfere with the undesired sound.

28 Claims, 7 Drawing Sheets

(56) References Cited

U.S. PATENT DOCUMENTS

| | | | | |
|---|---|---|---|---|
| 5,091,954 | A | 2/1992 | Sasaki et al. | 381/72 |
| 5,105,377 | A | 4/1992 | Ziegler, Jr. | 364/724.01 |
| 5,133,017 | A | 7/1992 | Cain et al. | 381/71 |
| 5,138,664 | A | 8/1992 | Kimura et al. | 381/72 |
| 5,170,433 | A | 12/1992 | Elliott et al. | |
| 5,182,774 | A | 1/1993 | Bourk | 381/71 |
| 5,208,868 | A | 5/1993 | Sapiejewski | 381/183 |
| 5,251,262 | A | 10/1993 | Suzuki et al. | 381/71 |
| 5,276,740 | A | 1/1994 | Inanaga et al. | 381/187 |
| 5,289,147 | A | 2/1994 | Koike et al. | 355/200 |
| 5,305,387 | A | 4/1994 | Sapiejewski | 381/71 |
| 5,321,759 | A * | 6/1994 | Yuan | 381/71.9 |
| 5,337,366 | A | 8/1994 | Eguchi et al. | 381/71 |
| 5,371,802 | A | 12/1994 | McDonald et al. | |
| 5,377,276 | A * | 12/1994 | Terai et al. | 381/71.11 |
| 5,381,473 | A | 1/1995 | Andrea et al. | 379/387 |
| 5,381,485 | A | 1/1995 | Elliott | |
| 5,400,409 | A | 3/1995 | Linhard | 381/92 |
| 5,425,105 | A | 6/1995 | Lo et al. | 381/71 |
| 5,427,102 | A | 6/1995 | Shimode et al. | 128/653.2 |
| 5,485,523 | A | 1/1996 | Tamamura et al. | 381/71 |
| 5,488,667 | A | 1/1996 | Tamamura et al. | 387/71 |
| 5,492,129 | A | 2/1996 | Greenberger | 128/715 |
| 5,493,616 | A | 2/1996 | Iidaka et al. | 381/71 |
| 5,497,426 | A | 3/1996 | Jay | 381/67 |
| 5,499,302 | A | 3/1996 | Nagami et al. | 381/71 |
| 5,526,421 | A | 6/1996 | Berger et al. | 379/389 |
| 5,559,893 | A | 9/1996 | Krokstad et al. | 381/71 |
| 5,586,189 | A | 12/1996 | Allie et al. | 381/71 |
| 5,602,927 | A | 2/1997 | Tamamura et al. | 381/71 |
| 5,602,928 | A | 2/1997 | Eriksson et al. | 381/71 |
| 5,602,929 | A | 2/1997 | Popovich | |
| 5,604,813 | A | 2/1997 | Evans et al. | 381/71 |
| 5,621,803 | A | 4/1997 | Laak | 381/71 |
| 5,673,325 | A | 9/1997 | Andrea et al. | 381/92 |
| 5,675,658 | A | 10/1997 | Brittain | 381/72 |
| 5,680,337 | A | 10/1997 | Pedersen et al. | 364/724.19 |
| 5,687,075 | A | 11/1997 | Stothers | |
| 5,689,572 | A | 11/1997 | Ohki et al. | 381/71.3 |
| 5,691,893 | A | 11/1997 | Stothers | |
| 5,692,059 | A | 11/1997 | Kruger | 381/151 |
| 5,699,437 | A | 12/1997 | Finn | |
| 5,706,344 | A | 1/1998 | Finn | 379/410 |
| 5,715,320 | A | 2/1998 | Allie et al. | 381/71.12 |
| 5,727,066 | A | 3/1998 | Elliott et al. | |
| 5,737,433 | A | 4/1998 | Gardner | 381/94.7 |
| 5,740,257 | A | 4/1998 | Marcus | 381/71.6 |
| 5,745,396 | A | 4/1998 | Shanbhag | 364/724.19 |
| 5,768,124 | A | 6/1998 | Stothers et al. | |
| 5,774,564 | A | 6/1998 | Eguchi et al. | 381/71.11 |
| 5,774,565 | A | 6/1998 | Benning et al. | 381/83 |
| 5,809,156 | A | 9/1998 | Bartels et al. | 381/183 |
| 5,815,582 | A | 9/1998 | Claybaugh et al. | 381/71.6 |
| 5,872,728 | A | 2/1999 | Richter | 364/724.2 |
| 5,937,070 | A | 8/1999 | Todter et al. | 381/71.6 |
| 6,069,959 | A | 5/2000 | Jones | 381/71.6 |
| 6,078,672 | A | 6/2000 | Saunders et al. | 381/71.6 |
| 6,163,610 | A | 12/2000 | Bartlett et al. | 379/433 |
| 6,166,573 | A | 12/2000 | Moore et al. | 327/161 |
| 6,181,801 | B1 | 1/2001 | Puthuff et al. | 381/380 |
| 6,185,299 | B1 | 2/2001 | Goldin | 379/406 |
| 6,278,785 | B1 | 8/2001 | Thomasson | 381/66 |
| 6,295,364 | B1 | 9/2001 | Finn et al. | 381/110 |
| 6,301,364 | B1 | 10/2001 | Lowmiller et al. | 381/66 |
| 6,337,680 | B1 | 1/2002 | Hamaji | 379/392.01 |
| 6,343,127 | B1 | 1/2002 | Billoud | 381/71.4 |
| 6,347,146 | B1 | 2/2002 | Short et al. | 381/15 |
| 6,421,443 | B1 | 7/2002 | Moore et al. | 379/406.01 |
| 6,445,799 | B1 | 9/2002 | Taenzer et al. | 381/71.6 |
| 6,445,805 | B1 | 9/2002 | Grugel | 381/330 |
| 6,466,673 | B1 | 10/2002 | Hardy | |
| 6,496,581 | B1 | 12/2002 | Finn et al. | 379/406.01 |
| 6,505,057 | B1 | 1/2003 | Finn et al. | 455/569 |
| 6,529,605 | B1 | 3/2003 | Christoph | |
| 6,532,289 | B1 | 3/2003 | Magid | 379/406.01 |
| 6,532,296 | B1 | 3/2003 | Vaudrey et al. | 381/371 |
| 6,567,524 | B1 | 5/2003 | Svean et al. | 381/71.1 |
| 6,567,525 | B1 | 5/2003 | Sapiejewski | 381/71.6 |
| 6,597,792 | B1 | 7/2003 | Sapiejewski et al. | 381/71.6 |
| 6,625,286 | B1 | 9/2003 | Rubacha et al. | 381/93 |
| 6,633,894 | B1 * | 10/2003 | Cole | 708/300 |
| 6,643,619 | B1 | 11/2003 | Linhard et al. | 704/233 |
| 6,665,410 | B1 | 12/2003 | Parkins | 381/71.1 |
| 6,687,669 | B1 | 2/2004 | Schrogmeier et al. | 704/226 |
| 6,690,800 | B2 | 2/2004 | Resnick | 381/73.1 |
| 6,798,881 | B2 | 9/2004 | Thomasson | 379/406.07 |
| 6,845,162 | B1 | 1/2005 | Emborg et al. | 381/71.4 |
| 6,991,289 | B2 | 1/2006 | House | 297/217.4 |
| 7,020,288 | B1 | 3/2006 | Ohashi | 381/71.4 |
| 7,062,049 | B1 | 6/2006 | Inoue et al. | 381/71.4 |
| 7,103,188 | B1 | 9/2006 | Jones | 381/71.9 |
| 7,133,529 | B2 | 11/2006 | Ura | 381/66 |
| 7,317,801 | B1 | 1/2008 | Amir | |
| 7,333,618 | B2 | 2/2008 | Shuttleworth et al. | 381/57 |
| 7,440,578 | B2 | 10/2008 | Arai et al. | 381/302 |
| 7,469,051 | B2 | 12/2008 | Sapashe et al. | 381/104 |
| 7,536,018 | B2 | 5/2009 | Onishi et al. | 381/71.8 |
| 7,574,006 | B2 | 8/2009 | Funayama et al. | 381/71.12 |
| 7,627,352 | B2 | 12/2009 | Gauger, Jr. et al. | 455/569.1 |
| 7,630,432 | B2 | 12/2009 | Hofmeister | 375/232 |
| 7,773,760 | B2 | 8/2010 | Sakamoto et al. | 381/71.9 |
| 7,808,395 | B2 | 10/2010 | Raisanen et al. | 340/667 |
| 7,873,173 | B2 | 1/2011 | Inoue et al. | 381/71.4 |
| 7,885,417 | B2 | 2/2011 | Christoph | 381/71.11 |
| 7,933,420 | B2 | 4/2011 | Copley et al. | 381/71.11 |
| 8,027,484 | B2 | 9/2011 | Yoshida et al. | 381/71.4 |
| 2001/0036283 | A1 | 11/2001 | Donaldson | 381/71.11 |
| 2002/0068617 | A1 | 6/2002 | Han | |
| 2002/0076059 | A1 | 6/2002 | Joynes | 381/71.6 |
| 2002/0138263 | A1 | 9/2002 | Deligne et al. | 704/233 |
| 2002/0143528 | A1 | 10/2002 | Deligne et al. | 704/224 |
| 2002/0172374 | A1 | 11/2002 | Bizjak | 381/71.14 |
| 2002/0176589 | A1 | 11/2002 | Buck et al. | 381/94.7 |
| 2003/0035551 | A1 | 2/2003 | Light et al. | 381/71.6 |
| 2003/0103636 | A1 | 6/2003 | Arai et al. | 381/302 |
| 2003/0142841 | A1 | 7/2003 | Wiegand | 381/172 |
| 2003/0228019 | A1 | 12/2003 | Eichler et al. | 381/71.8 |
| 2004/0037429 | A1 | 2/2004 | Candioty | 381/67 |
| 2004/0076302 | A1 | 4/2004 | Christoph | 381/57 |
| 2005/0063552 | A1 | 3/2005 | Shuttleworth et al. | |
| 2005/0175187 | A1 * | 8/2005 | Wright et al. | 381/71.12 |
| 2005/0207585 | A1 | 9/2005 | Christoph | 381/71.11 |
| 2005/0226434 | A1 | 10/2005 | Franz et al. | 381/71.7 |
| 2005/0232435 | A1 | 10/2005 | Stothers et al. | |
| 2006/0098809 | A1 * | 5/2006 | Nongpiur et al. | 379/406.14 |
| 2006/0153394 | A1 | 7/2006 | Beasley | 381/57 |
| 2006/0251266 | A1 | 11/2006 | Saunders et al. | 381/71.1 |
| 2006/0262935 | A1 | 11/2006 | Goose et al. | 381/17 |
| 2007/0053532 | A1 | 3/2007 | Elliott et al. | |
| 2007/0098119 | A1 | 5/2007 | Stothers et al. | |
| 2007/0253567 | A1 | 11/2007 | Sapiejewski | 381/71.6 |
| 2007/0274531 | A1 | 11/2007 | Camp | 381/74 |
| 2008/0095383 | A1 | 4/2008 | Pan et al. | 381/71.11 |
| 2008/0152158 | A1 | 6/2008 | Sakamoto et al. | |
| 2008/0181422 | A1 | 7/2008 | Christoph | 381/73.1 |
| 2008/0192948 | A1 | 8/2008 | Kan et al. | 381/71.4 |
| 2008/0247560 | A1 | 10/2008 | Fukuda et al. | 381/71.6 |
| 2009/0067638 | A1 | 3/2009 | Sakamoto et al. | 381/71.4 |
| 2009/0086990 | A1 | 4/2009 | Christoph | 381/71.12 |
| 2009/0086995 | A1 | 4/2009 | Christoph et al. | |
| 2009/0220102 | A1 | 9/2009 | Pan et al. | 381/71.11 |
| 2009/0279710 | A1 | 11/2009 | Onishi et al. | |
| 2010/0002892 | A1 | 1/2010 | Togawa et al. | |
| 2010/0014685 | A1 | 1/2010 | Wurm | 381/71.11 |
| 2010/0061566 | A1 | 3/2010 | Moon et al. | 381/71.8 |
| 2010/0098263 | A1 | 4/2010 | Pan et al. | 381/71.11 |
| 2010/0098265 | A1 | 4/2010 | Pan et al. | 381/94.1 |
| 2010/0124336 | A1 | 5/2010 | Shridhar et al. | 371/71.4 |
| 2010/0124337 | A1 | 5/2010 | Wertz et al. | 381/71.11 |
| 2010/0226505 | A1 | 9/2010 | Kimura | 381/71.6 |
| 2010/0239105 | A1 | 9/2010 | Pan | 381/94.9 |
| 2010/0260345 | A1 | 10/2010 | Shridhar et al. | 381/71.1 |
| 2010/0266134 | A1 | 10/2010 | Wertz et al. | 381/71.1 |
| 2010/0266137 | A1 | 10/2010 | Sibbald et al. | 381/71.6 |

(56) References Cited

U.S. PATENT DOCUMENTS

| | | | | |
|---|---|---|---|---|
| 2010/0272275 | A1 | 10/2010 | Carreras et al. | |
| 2010/0272276 | A1 | 10/2010 | Carreras et al. | 381/71.6 |
| 2010/0272280 | A1 | 10/2010 | Joho et al. | 381/71.6 |
| 2010/0272281 | A1 | 10/2010 | Carreras et al. | 381/71.6 |
| 2010/0274564 | A1 | 10/2010 | Bakalos et al. | 704/500 |
| 2010/0290635 | A1 | 11/2010 | Shridhar et al. | 381/71.1 |
| 2010/0296669 | A1 | 11/2010 | Oh et al. | 381/109 |
| 2011/0116643 | A1 | 5/2011 | Tiscareno et al. | 381/58 |
| 2012/0170763 | A1 | 7/2012 | Shridhar et al. | 381/71.1 |
| 2012/0170764 | A1 | 7/2012 | Shridhar et al. | 381/71.1 |

FOREIGN PATENT DOCUMENTS

| | | | | |
|---|---|---|---|---|
| EP | 0 539 940 | B1 | 4/1996 | |
| EP | 0 572 492 | B1 | 11/1997 | |
| EP | 0 898 266 | A2 | 2/1999 | |
| EP | 1 653 445 | A1 | 5/2006 | G10L 21/02 |
| EP | 1 577 879 | B1 | 7/2008 | |
| EP | 1 947 642 | A1 | 7/2008 | |
| EP | 2 133 866 | A1 | 12/2009 | |
| EP | 2 284 831 | A1 | 2/2011 | |
| GB | 2 293 898 | B | 4/1996 | |
| JP | 61-112496 | | 5/1986 | H04R 3/00 |
| JP | 5-011772 | | 1/1993 | |
| JP | 5-173581 | | 7/1993 | |
| JP | 6-118968 | | 4/1994 | |
| JP | 06-318085 | | 11/1994 | |
| JP | 06-332474 | | 12/1994 | G10K 11/16 |
| JP | 07-056583 | | 3/1995 | G10K 11/178 |
| JP | 08-095579 | | 4/1996 | G10K 11/78 |
| JP | 08-234767 | | 9/1996 | |
| JP | 10-207470 | | 8/1998 | G10K 11/178 |
| JP | 11 259078 | A | 9/1999 | |
| JP | 2000-330572 | | 11/2000 | |
| JP | 2006-126841 | | 5/2006 | G10L 21/02 |
| JP | 2007-243739 | | 9/2007 | |
| JP | 2007-253799 | | 10/2007 | B60R 11/02 |
| WO | WO 90/09655 | | 8/1990 | |
| WO | WO 94/09480 | | 4/1994 | |
| WO | WO 94/09481 | | 4/1994 | |
| WO | WO 94/09482 | | 4/1994 | |
| WO | WO 95/09415 | | 4/1995 | |
| WO | WO 95/26521 | | 10/1995 | |
| WO | WO 96/10780 | | 4/1996 | |
| WO | WO 2007/011010 | A1 | 1/2007 | |
| WO | WO 2008/126287 | A1 | 10/2008 | |

OTHER PUBLICATIONS

Martins C R et al., "Fast Adaptive Noise Canceller Using the LMS Algorithm", Proceedings of the International Conference on Signal Processing Applications and Technology, vol. 1, Sep. 28, 1993, 7 pgs.

European Search Report from European Application No. EP 10162225, dated Oct. 1, 2010, 5 pgs.

Gonzalez, A. et al., "Minimisation of the maximum error signal in active control", IEEE International Conference on Acoustics, Speech, and Signal Processing, 1997, 4 pgs.

Colin H. Hansen et al., "Active Control of Noise and Vibration," E & FN Spon., London SE1, Copyright 1997, pp. 642-652.

Gao, F. X. Y. et al., "An Adaptive Backpropagation Cascade IIR Filter," *IEEE*, vol. 39, No. 9, 1992, pp. 606-610.

Kuo, S. M. et al., "Active Noise Control Systems: Algorithms and DSP Implementations," John Wiley & Sons, Inc., New York, NY, Copyright 1996, pp. 88-97.

Notice of Allowance, dated Nov. 2, 2011, pp. 1-9, U.S. Appl. No. 12/275,118, U.S. Patent and Trademark Office, Virginia.

Office Action, dated Aug. 26, 2011, pp. 1-24, U.S. Appl. No. 12/421,459, U.S. Patent and Trademark Office, Virginia.

Office Action, dated Jul. 25, 2011, pp. 1-11, U.S. Appl. No. 12/275,118, U.S. Patent and Trademark Office, Virginia.

Office Action, dated Aug. 17, 2011, pp. 1-26, U.S. Appl. No. 12/425,997, U.S. Patent and Trademark Office, Virginia.

Office Action, dated Sep. 13, 2011, pp. 1-16, U.S. Appl. No. 12/420,658, U.S. Patent and Trademark Office, Virginia.

Notice of Allowance, dated Aug. 15, 2011, pp. 1-14, U.S. Appl. No. 12/466,282, U.S. Patent and Trademark Office, Virginia.

Chen, Kean et al., Adaptive Active Noise Elimination and Filter-XLMS Algorithm, 1993, pp. 27-33, vol. 12 (4), Applied Acoustics, and translation of Abstract (8 pgs.).

Kuo, Sen M. et al., Active Noise Control: A Tutorial Review, Jun. 1999, pp. 943-972, vol. 87, No. 6, Proceedings of the IEEE.

Chinese Office Action, dated Jul. 31, 2012, pp. 1-10, Chinese Patent Application No. 201010003225.4, Chinese Patent Office, China.

Notice of Allowance, dated Feb. 2, 2012, U.S. Appl. No. 12/421,459, U.S. Patent and Trademark Office, Virginia.

Kuo, S. M. et al., "Active Noise Control Systems: Algorithms and DSP Implementations," John Wiley & Sons, Inc., New York, NY, Copyright 1996, 418 pgs.

Notice of Allowance, dated Jan. 13, 2012, U.S. Appl. No. 12/425,997, U.S. Patent and Trademark Office, Virginia.

Office Action, dated Mar. 7, 2012, pp. 1-13, U.S. Appl. No. 12/420,658, U.S. Patent and Trademark Office, Virginia.

Japanese Office Action mailed May 14, 2012, Japanese Patent Application No. 2009-293510, 7 pgs.

Notice of Allowance, dated Jul. 16, 2012, pp. 1-14, U.S. Appl. No. 13/418,095 U.S. Patent and Trademark Office, Virginia.

Office Action, dated May 25, 2012, pp. 1-12, U.S. Appl. No. 12/420,658, U.S. Patent and Trademark Office, Virginia.

Notice of Allowance, dated May 15, 2012, pp. 1-7, U.S. Appl. No. 13/419,420 U.S. Patent and Trademark Office, Virginia.

* cited by examiner

SYSTEM FOR ACTIVE NOISE CONTROL WITH PARALLEL ADAPTIVE FILTER CONFIGURATION

BACKGROUND OF THE INVENTION

1. Technical Field

This invention relates to active noise control, and more specifically to active noise control using a plurality of adaptive filters.

2. Related Art

Active noise control may be used to generate sound waves that destructively interfere with a targeted undesired sound. The destructively interfering sound waves may be produced through a loudspeaker to combine with the targeted undesired sound.

An active noise control system generally includes a plurality of adaptive filters each receiving a particular frequency range associated with an undesired sound. The particular frequency range may be provided to each adaptive filter using a plurality of bandpass filters. Thus, processing time may be involved to filter the undesired sound with the bandpass filters and subsequently processing the undesired sound with an adaptive filter. This processing time may decrease efficiency associated with generating destructively interfering sound waves. Therefore, a need exists to increase efficiency in generating destructively interfering sound waves in an active noise control system.

SUMMARY

The present disclosure addresses the above need by providing a system and method for anti-noise generation with an ANC system implementing a plurality of adaptive filters.

An active noise control system may implement a plurality of adaptive filters each configured to receive a common input signal representative of an undesired sound. Each adaptive filter may converge to generate an output signal based on the common input signal and a respective update signal. The output signals of the adaptive filters may be used to generate an anti-noise signal that may drive a loudspeaker to generate sound waves to destructively interfere with the undesired sound. Each output signal may be independently adjusted base on an error signal.

The adaptive filters may each have different respective filter length. Each filter length may correspond to a predetermined frequency range. Each adaptive filter may converge more quickly relative to the other adaptive filters depending on the frequency range of the input signal. One or more adaptive filters may converge prior to the other adaptive filters allowing an output signals from the first converging filter or filters to be used as an anti-noise signal.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

An active noise control system may be configured to generate a destructively interfering sound wave. This is accomplished generally by first determining presence of an undesired sound and generating a destructively interfering sound wave. The destructively interfering sound wave may be transmitted as speaker output. A microphone may receive sound waves from the speaker output and the undesired sound. The microphone may generate an error signal based on the sound waves. The active noise control system may include a plurality of adaptive filters each configured to receive a signal representative of the undesired sound. The plurality of adaptive filters may operate in parallel to each generate an output signal. The output signals of each of the adaptive filters may be summed together to generate a signal to drive to the speaker.

Figure 1:
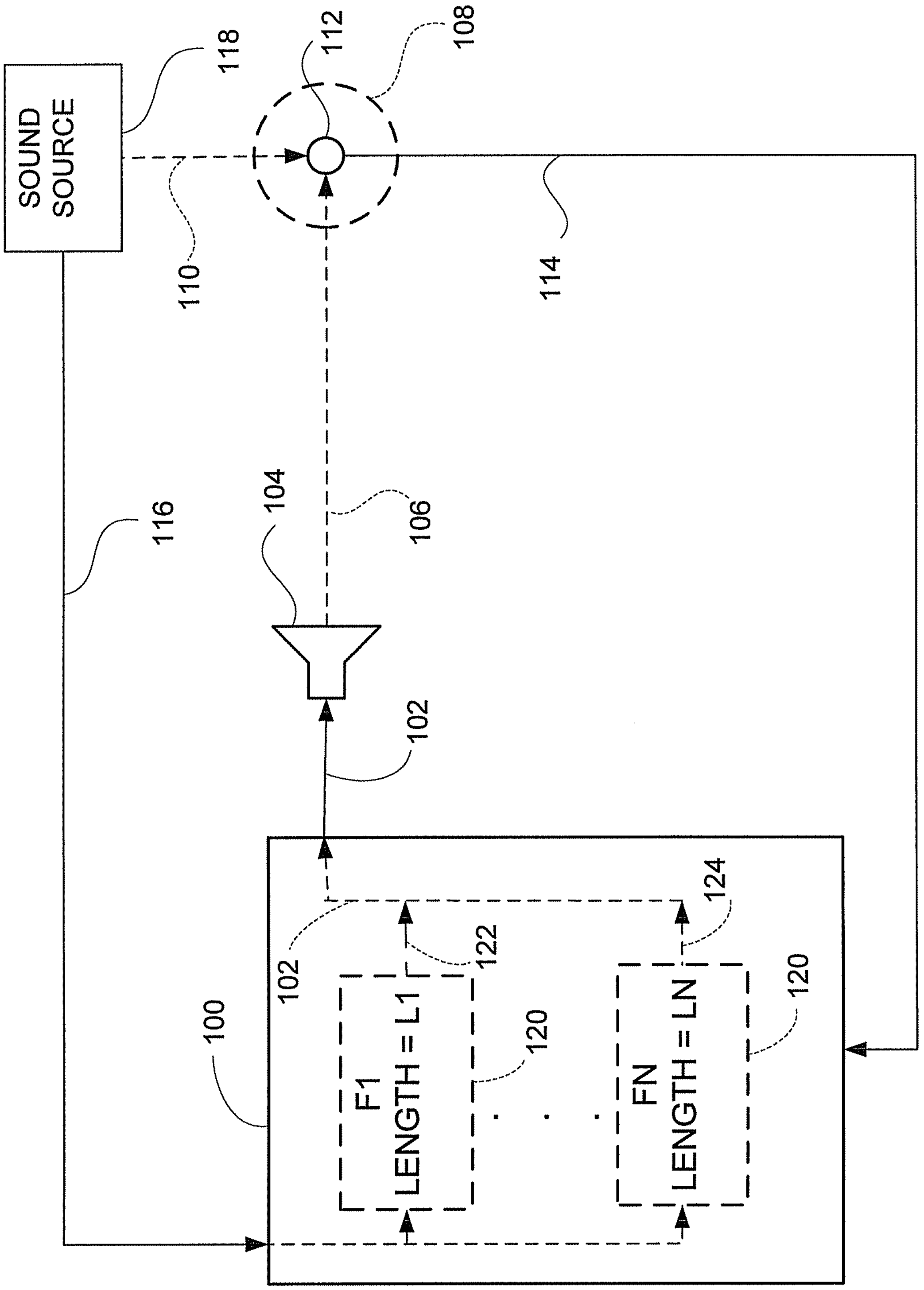
FIG. 1 is a diagrammatic view of an example active noise cancellation (ANC) system.

In FIG. 1, an example active noise control (ANC) system 100 is diagrammatically shown. The ANC system 100 may be used to generate an anti-noise signal 102, which may be provided to drive a speaker 104 to produce sound waves as speaker output 106. The speaker output 106 may be transmitted to a target space 108 to destructively interfere with an undesired sound 110 present in a target space 108. In one example, anti-noise may be defined by sound waves of approximately equal amplitude and frequency and approximately 180 degrees out of phase with the undesired sound 110. The 180 degree shift of the anti-noise signal will cause destructive interference with the undesired sound in an area in which the anti-noise sound waves and the undesired sound 110 sound waves combine such as the target space 108. The ANC system 100 may be configured to generate anti-noise associated with various environments. For example, the ANC system 100 may be used to reduce or eliminate sound present in a vehicle. A target space may be selected in which to reduce or eliminate sounds related to vehicle operation such as engine noise or road noise. In one example, the ANC system 100 may be configured to eliminate an undesired sound with a frequency range of approximately 20-500 Hz.

A microphone 112 may be positioned within the target space 108 to detect sound waves present in the target space 108. In one example, the target space 108 may detect sound waves generated from the combination of the speaker output 106 and the undesired sound 110. The detection of the sound waves by the microphone 112 may cause an error signal 114 to be generated. An input signal 116 may also be provided to the ANC system 100, which may be representative of the undesired sound 110 emanating from a sound source 118. The ANC system 100 may generate the anti-noise signal 102 based on the input signal 116. The ANC system 100 may use the error signal 114 to adjust the anti-noise signal 102 to more accurately cause destructive interference with the undesired sound 110 in the target space 108.

In one example, the ANC system 100 may include a plurality of adaptive filters 120 configured in parallel to one another. In FIG. 1, the ANC system 100 may include N filters, with each filter being individually designated as F1 through FN. Each filter 120 may have a different respective filter length L1 through LN. The filter length of each filter 120 may determine how quickly a filter 120 converges, or provides a desired output, depending on the frequencies associated with an input signal. In one example, filter length of each filter 120 may correspond to a particular frequency range. The undesired sound x(n) may include a dominant signal component within a particular frequency range. The signal component may be "dominant" in the sense that the amplitude of the dominant component is higher at a frequency or within a frequency range than amplitudes of other frequency-based components of the undesired sound x(n). Each filter 120 may converge faster relative to the other filters when the dominant signal component is within a particular frequency range of a corresponding filter 120. The filter lengths may be chosen so that the corresponding frequency ranges overlap among the adaptive filters 120.

In FIG. 1, the input signal 116 is provided directly to each filter 120. Each filter 120 may generate an output signal in an attempt to generate an anti-noise signal based on the same input signal 116. For example, filters F1 and FN may attempt to converge in order to generate the anti-noise signal 102 based on the input signal 116. Each filter F1 and FN may generate an output signal 122 and 124, respectively. The output signals 122 and 124 may be provided to the speaker 104. One of the filters F1 and FN may contribute more significantly in generating a desired output signal relative to the other filters, regardless of convergence speed. However, each filter F1 through FN may generate a portion of the desired output signal allowing the combination of each filter 120 output to be combined in order to form the desired anti-noise signal 102.

Figure 2:
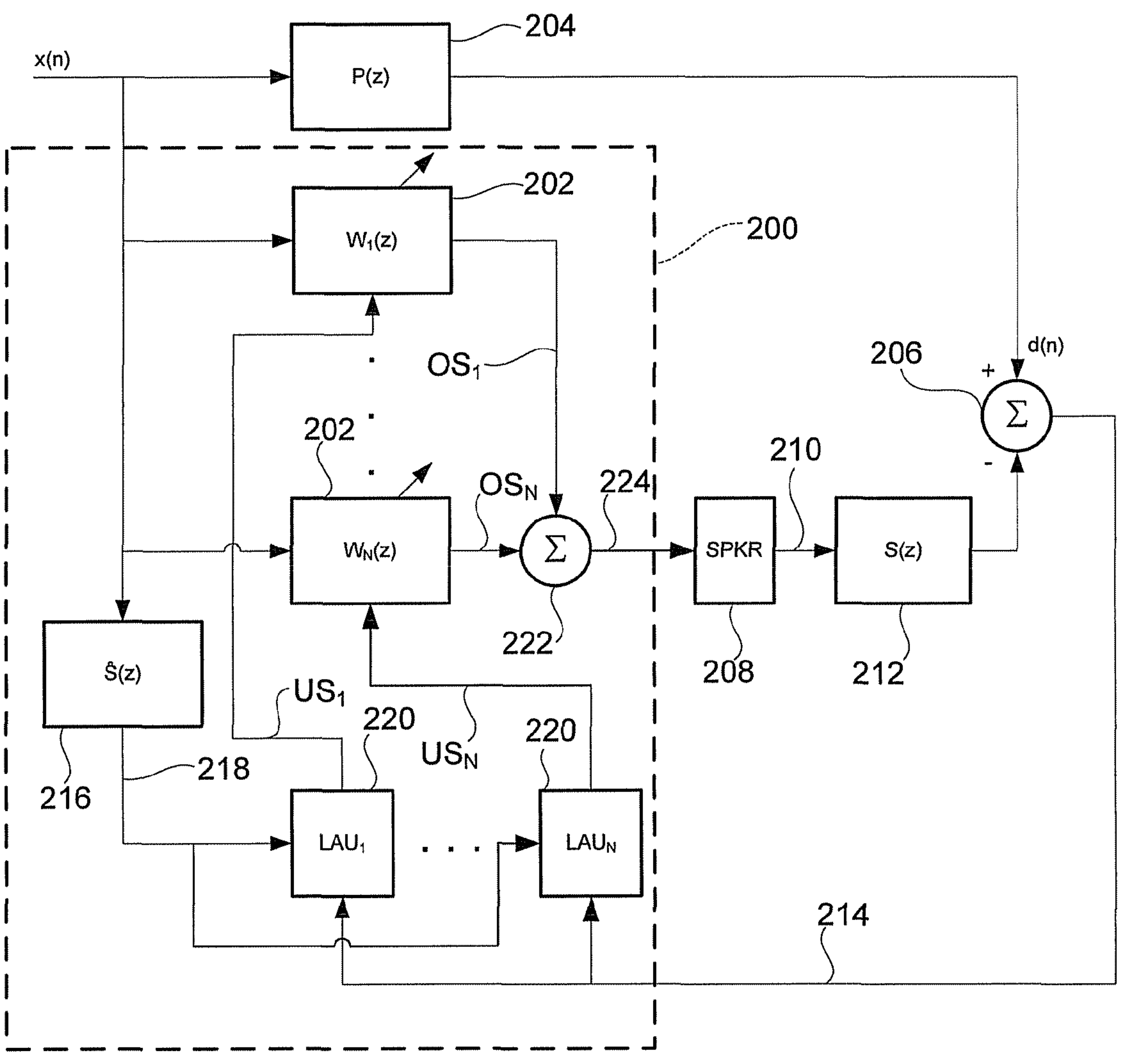
FIG. 2 is a block diagram of an example configuration implementing an ANC system.

In FIG. 2, an ANC system 200 is shown in a Z-domain block diagram format. The ANC system 200 may include a plurality of adaptive filters 202, which may be digital filters having different filter lengths. In the example shown in FIG. 2, the plurality of adaptive filters 202 may be individually denoted as Z-domain transfer functions $W_1(z)$ through $W_N(z)$, where N may be the total number of filters 202 used in the ANC system 200. Similar to that described in FIG. 1, the ANC system 200 may be used to generate an anti-noise signal that may be transmitted to a target space in order to destructively interfere with an undesired sound d(n), which may be the condition of an undesired sound x(n) after traversing a physical path. The undesired sound x(n) and d(n) is denoted as being in the digital domain in FIG. 2, however, for purposes of FIG. 2, x(n) and d(n) may each represent both a digital and analog-based signal of the undesired sound.

The undesired sound x(n) is shown as traversing a physical path 204 to a microphone 206, which may be positioned within or proximate to a space targeted for anti-noise to destructively interfere with the undesired sound d(n). The physical path 204 may be represented by a Z-domain transfer function P(z) in FIG. 2. A speaker 208 may generate speaker output 210 based on an anti-noise signal to destructively interfere with the undesired sound. The speaker output 210 may traverse a physical path 212 from the speaker to the microphone 206. The physical path 212 may be represented by a Z-domain transfer function S(z) in FIG. 2.

The microphone 206 may detect sound waves within a targeted space. The microphone 206 may generate an error signal 214 based on the detected sound waves. The error signal 214 may represent any sound remaining after the speaker output 210 destructively interferes with the undesired noise d(n). The error signal 214 may be provided to the ANC system 200.

In FIG. 2, the undesired sound x(n) may be provided to the ANC system 200 to generate anti-noise, which may be provided through microphone output generated based on the undesired sound or other sensor that generates a reference signal indicative of the undesired sound x(n). The undesired sound x(n) may be provided directly and in parallel to each of the adaptive filters 202. The undesired sound x(n) may also be filtered through an estimated path filter 216, designated as Z-domain transfer function $\hat{S}(z)$ in FIG. 2. The estimated path filter 216 may filter the undesired sound x(n) to estimate an effect that the undesired noise may experience if traversing between the speaker 208 and the microphone 206. The filtered undesired sound 218 is provided to a plurality of learning algorithm units (LAUs) 220. In one example, each LAU 220 may implement least mean squares (LMS), normalized least mean squares (NLMS), recursive least mean squares (RLMS), or any other suitable learning algorithm. In FIG. 2, each LAU 220 is individually denoted as $LAU_1$-$LAU_N$, where N may be the total number of LAUs 220. Each LAU 220 may provide an update signal (US) to a corresponding adaptive filter 202. For example, in FIG. 2, each LAU 220 is shown as providing a respective update signal $US_1$-$US_N$ to a corresponding filter 202. Each LAU 220 may generate an update signal based on the received filtered undesired sound signal 218 and error signal 214.

In one example, each of the adaptive filters 202 may be a digital filter having different filter lengths from one another, which may allow each filter 202 to converge faster for an input signal having a particular frequency range relative to the other filters 202. For example, the filter $W_1(z)$ may be shorter in length than the filter $W_N(z)$. Thus, if an input signal of a relatively high frequency is input into the plurality of adaptive filters 202, the filter $W_1(z)$ may be configured to converge more quickly than the other filters 202. However, each adaptive filter 202 may attempt to converge based on the input signal allowing each filter 202 to contribute at least a portion of the desired anti-noise signal. Similarly, if an input signal has a relatively low frequency and is input to the adaptive filters 202, the filter $W_N(z)$ may be configured to converge more quickly relative to the other filters 202. As a result, the filter $W_N(z)$ may begin to contribute at least a portion of the desired anti-noise signal prior to other adaptive filters.

Output signals $OS_1$-$OS_N$ of the adaptive filters 202 may be adjusted based on the received update signal. For example, the undesired sound x(n) may be time varying so that it may exist at different frequencies over time. The adaptive filters 202 may receive the undesired sound x(n) and a respective update signal, which may provide adjustment information allowing each adaptive filter 202 to adjust its respective output signal $OS_1$-$OS_N$.

The output signals $OS_1$-$OS_N$ may be summed at a summation operation 222. An output signal 224 of the summation operation 222 may be the anti-noise signal. The anti-noise signal 224 may drive the speaker 208 to produce the speaker output 210, which may be used to destructively interfere with the undesired sound x(n). In one example the adaptive filters 202 may be configured to directly generate an anti-noise signal. In alternative examples, the adaptive filters 202 may be configured to emulate the undesired sound x(n) with the output signals $OS_1$-$OS_N$ with the anti-noise signal 124 being inverted prior to driving the speaker 208 or the output signals $OS_1$-$OS_N$ may be inverted prior to the summation operation 222.

Summing the output signals $OS_1$-$OS_N$ allows all of the outputs to be provided to the speaker 208. As each of the adaptive filters 202 attempt to converge in generating anti-noise based on the undesired sound x(n) and a respective update signal, each filter 202 may be configured to converge faster relative to the other filters 202, as previously discussed, due to the varying filter lengths. Thus, one or more of the filters 202 may generate a portion of the desired anti-noise more quickly relative to the other adaptive filters 202. However, each filter 202 may contribute at least a portion of the anti-noise allowing the summation of the outputs signals $OS_1$-$OS_N$ at the summation operation 222 to result in the desired anti-noise signal 224. Thus, the configuration shown in FIG. 2 allows all of the adaptive filter output signals $OS_1$-$OS_N$ to be passed to the speaker 208, with any filter 202 generating the desired anti-noise signal as an output signal having that output signal drive the speaker 208 to produce the desired anti-noise.

Figure 3:
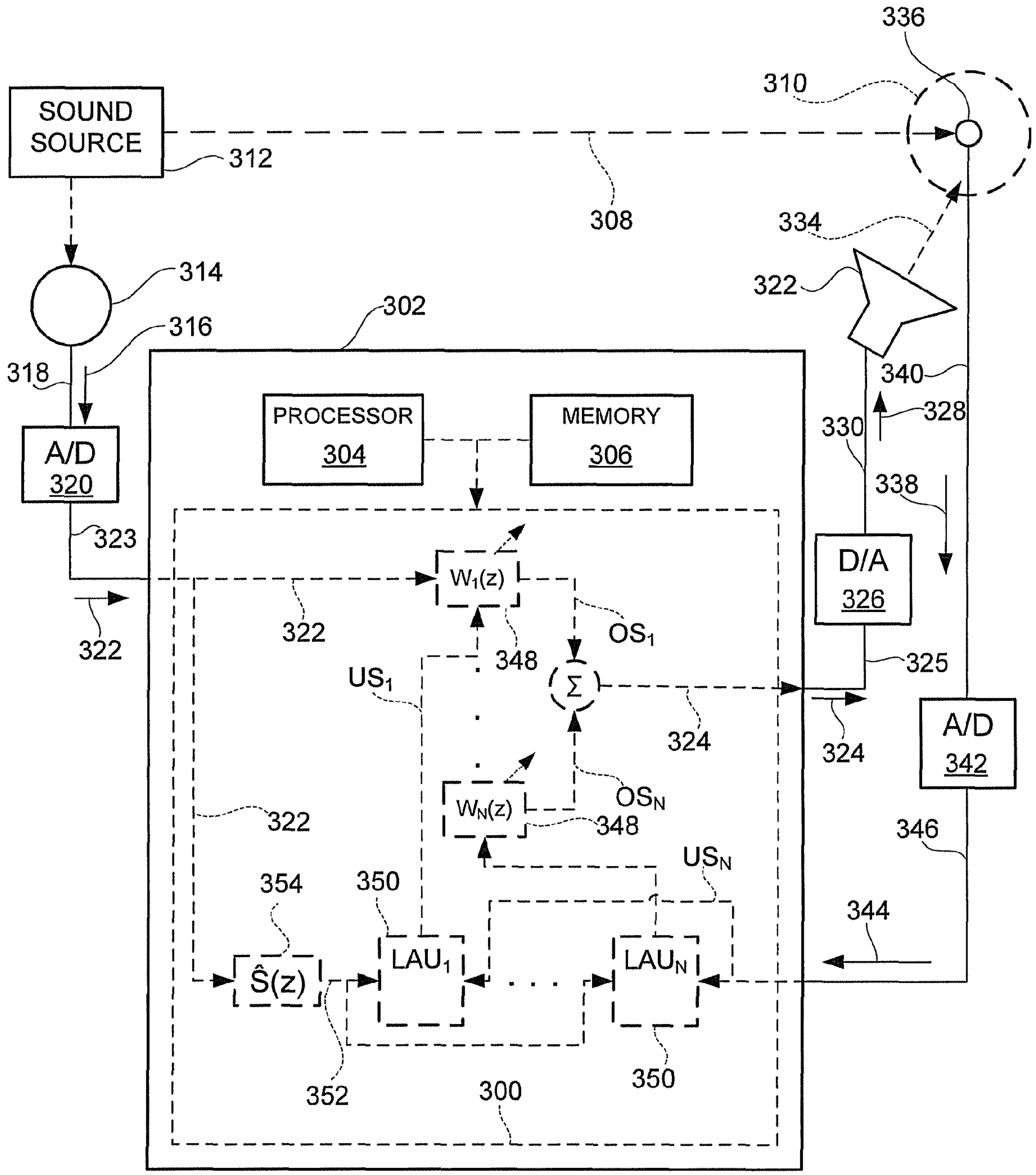
FIG. 3 is an example ANC system.

FIG. 3 shows an example of an ANC system 300 that may be implemented on a computer device 302. The computer device 302 may include a processor 304 and a memory 306, which may be implemented to generate a software-based ANC system, such as the ANC system 300. The ANC system 300 may be implemented as instructions on the memory 306 executable by the processor 304. The memory 306 may be computer-readable storage media or memories, such as a cache, buffer, RAM, removable media, hard drive or other computer readable storage media. Computer readable storage media include various types of volatile and nonvolatile storage media. Various processing techniques may be implemented by the processor 304 such as multiprocessing, multitasking, parallel processing and the like, for example.

The ANC system 300 may be implemented to generate anti-noise to destructively interfere with an undesired sound 308 in a target space 310. The undesired sound 308 may emanate from a sound source 312. A sensor 314 may detect the undesired sound 308. The sensor 314 may be various forms of detection devices depending on a particular ANC implementation. For example, the ANC system 300 may be configured to generate anti-noise in a vehicle to destructively interfere with engine noise. The sensor 314 may be an accelerometer or vibration monitor configured to generate a signal based on the engine noise. The sensor 314 may also be a microphone configured to directly receive the engine noise in order to generate a representative signal for use by the ANC system 300. In other examples, any other undesirable sound may be detected within a vehicle, such as fan or road noise. The sensor 314 may generate an analog-based signal 316 representative of the undesired sound that may be transmitted through a connection 318 to an analog-to-digital (A/D) converter 320. The A/D converter 320 may digitize the signal 316 and transmit the digitized signal 322 to the computer device 302 through a connection 323. In an alternative example, the A/D converter 320 may be instructions stored on the memory 306 that are executable by the processor 304.

The ANC system 300 may generate an anti-noise signal 324 that may be transmitted through a connection 325 to a digital-to-analog (D/A) converter 326, which may generate an analog-based anti-noise signal 328 that may be transmitted through a connection 330 to a speaker 332 to drive the speaker to produce anti-noise sound waves as speaker output 334. The speaker output 334 may be transmitted to the target space 310 to destructively interfere with the undesired sound 308. In an alternative example, the D/A converter 326 may be instructions stored on the memory 306 and executed by the processor 304.

A microphone 336 or other sensing device may be positioned within the target space 310 to detect sound waves present within and proximate to the target space 310. The microphone 336 may detect sound waves remaining after occurrence of destructive interference between the speaker output 334 of anti-noise and the undesired sound 308. The microphone 336 may generate a signal 338 indicative of the detected sound waves. The signal 338 may be transmitted through a connection 340 to an A/D converter 342 where the signal may be digitized as signal 344 and transmitted through a connection 346 to the computer 302. The signal 344 may represent an error signal similar to that discussed in regard to FIGS. 1 and 2. In an alternative example, the A/D converter 342 may be instructions stored on the memory 306 and executed by the processor 304.

The processor 304 and memory 306 may operate within the ANC system 300. As shown in FIG. 3, the ANC system 300 may operate in a manner similar to that described in regard to FIG. 2. For example, the ANC system 300 may include a plurality of adaptive filters 348, which are each individually denoted as $W_1(z)$-$W_N(z)$, where N may be the total number of adaptive filters 348 in the ANC system 300.

The ANC system 300 may also include a number of LAUs 350, with each LAU 350 individually designated as $LAU_1$-$LAU_N$. Each LAU 350 may correspond to one of the adaptive filters 348 and provide a corresponding update signal $US_1$-$US_N$. Each LAU 350 may generate an update signal based on the error signal 344 and a signal 352, which may be the undesired sound signal 322 filtered by an estimated path filter 354 designated as $\hat{S}(z)$. Each adaptive filter 348 may receive the undesired sound signal 322 and an update signal, $US_1$-$US_N$, respectively, to generate an output signal $OS_1$-$OS_N$. The output signals $OS_1$-$OS_N$ may be summed together through a summation operation 356, the output of which may be the anti-noise signal 324, and may be output from the computer 302.

As discussed in regard to FIG. 2, the plurality of adaptive filters 348 may each be configured to have different filter lengths, and thus may each be configured to converge more quickly to generate a desired output in a predetermined input frequency range as compared to one another. In one example, the adaptive filters 348 may be finite impulse response (FIR) filters, with the length of each filter 348 depending on the number of filter coefficients. Each adaptive filter 348 may receive the undesired noise signal 322 with each adaptive filter 348 attempting to produce the appropriate anti-noise. Due to the varying filter lengths of the adaptive filters 348, the adaptive filters may each be configured to converge, or reach a desired output of anti-noise, at different rates or windows of time relative to the other adaptive filters 348 depending on the frequency range of the input signal. One of the adaptive filters 348 may contribute more significantly to producing anti-noise relative to the other adaptive filters 348 for an input signal having a particular frequency or frequency range, regardless of convergence speed. However, as previously discussed, the other adaptive filters 348 may contribute a portion of the desired anti-noise allowing the respective output signal $OS_1$ through $OS_N$ to be summed with one another to produce the desired anti-noise. Once the appropriate anti-noise is generated, each adaptive filter 348 will receive an error signal of approximately zero. Thus, each adaptive filter 348 will maintain its current output when the respective error signal is zero, allowing the appropriate anti-noise to be constantly generated until the undesired sound x(n) changes, causing the filters 348 to each adjust output.

Figure 4:
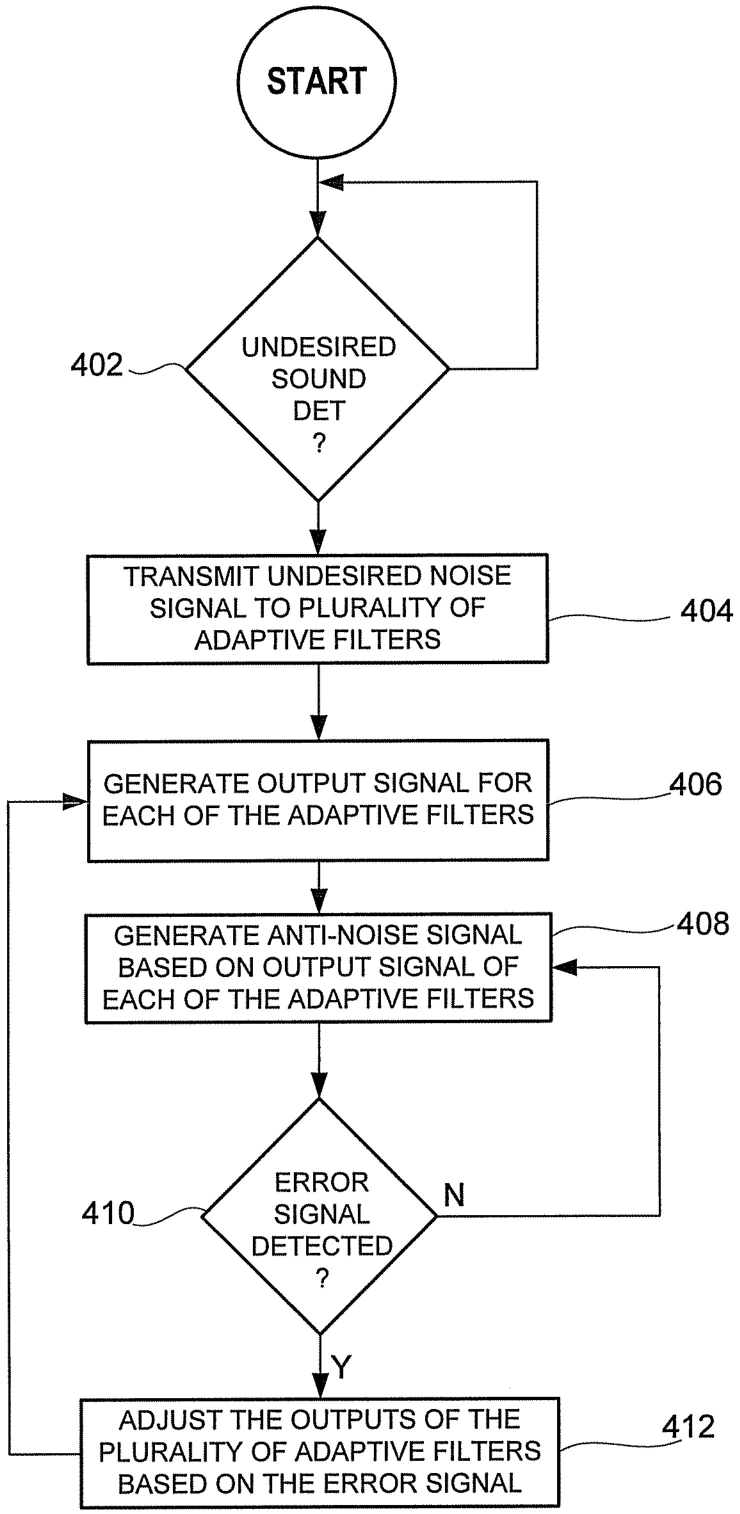
FIG. 4 is a flowchart of an example operation of generating anti-noise.

FIG. 4 shows a flowchart of an example operation to generate anti-noise using a plurality of adaptive filters such as that described in FIGS. 2 and 3. A step 402 may include detecting an undesired noise. In one example, step 402 may represent a sensor, such as the sensor 314, which may be configured to receive an undesired sound at any time. Thus, detection of the undesired sound may refer to the presence of the undesired sound being received by the sensor 314. If no undesired sound is detected, or present, step 402 may be continuously performed until a present undesired sound is detected by a sensor. Upon detection of the undesired sound, a step 404 of transmitting the undesired sound to a plurality of adaptive filters may be performed. In one example, step 404 may be performed in the manner described in regard to FIG. 3, such as digitizing the undesired sound signal 316 and transmitting the digitized signal 322 to the plurality of adaptive filters 348.

The operation may also include a step 406 of generating an output signal for each of the plurality of filters. In one example, step 406 may be performed through generating an output signal for each of a plurality of adaptive filters using an undesired noise as an input signal to each of the adaptive filters, such as described in regard to FIG. 3. Upon generation of the output signals, a step 408 may include generating an anti-noise signal based on the output signal of each of the adaptive filters. In one example, step 408 may be performed by summing each output signal of the plurality of adaptive filters, such as summing the output signals $OS_1$-$OS_N$ shown in FIG. 3. The summed output signals may represent the anti-noise signal.

The operation may include a step 410 of determining the presence of an error signal. In one example, step 410 may be performed through use of a sensor input signal, such as a microphone input signal, as shown in FIG. 3. If an error signal is not detected, step 408 may be continuously performed, which will continue to generate an anti-noise signal for a current undesired sound. If an error signal is detected, a step 412 of adjusting the outputs of the adaptive filters based on the error signal may be performed. In one example, this step may be performed through use of LAUs, such as that described in regard to FIG. 3. The adaptive filters 348 in FIG. 3 each have an associated LAU 350, which receives the error signal 324 and a filtered signal 352 representative of the undesired sound. The LAUs 350 each provide an update signal to the respective adaptive filter 348 allowing the adaptive filter 348 to adjust its output based on the error signal 324 in an effort to converge based on the input signal to produce an output signal that successfully cancels the undesired noise.

Figure 5:
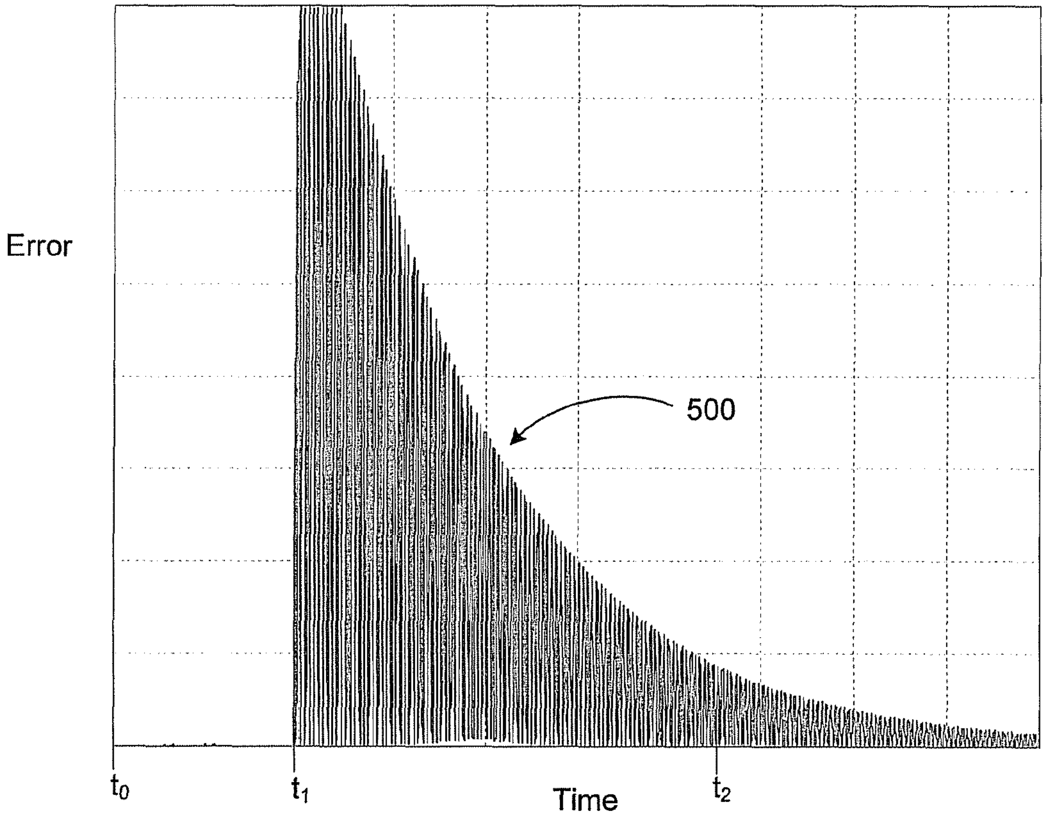
FIG. 5 is a plot of an error signal over time for an ANC system implementing a single adaptive filter.
Figure 6:
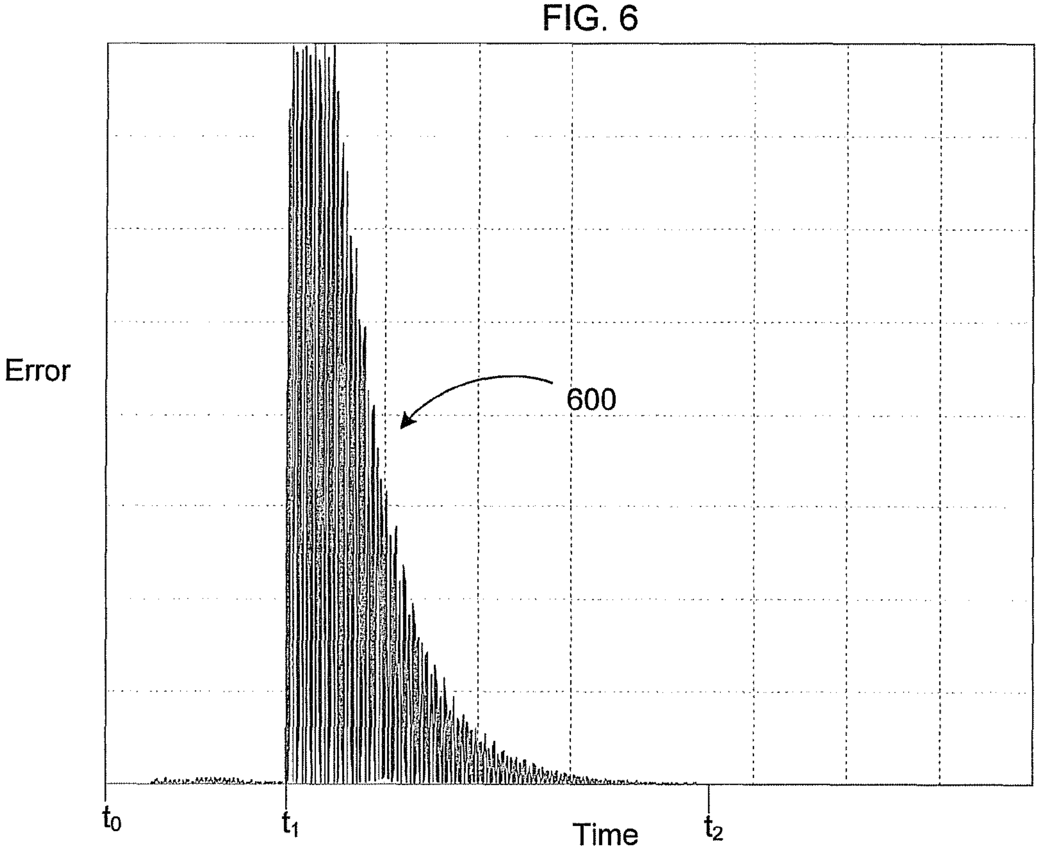
FIG. 6 is a plot of an error signal over time for an ANC system implementing a plurality of adaptive filters.

FIGS. 5-9 show a number of plots associated with an example ANC system. In one example, an ANC system may include three adaptive filters $W_1$, $W_2$, and $W_3$, each having a varying filter length. Each filter may receive an input signal of an undesired sound. FIG. 5 shows a plot of an error signal 500, such as that detected by the microphone 336 in FIG. 4. In FIG. 5, the error signal 500 is shown for an ANC system having one adaptive filter. In FIG. 6, an error signal 600 is shown for an ANC system implementing the adaptive filters $W_1$, $W_2$, and $W_3$.

Figure 7:
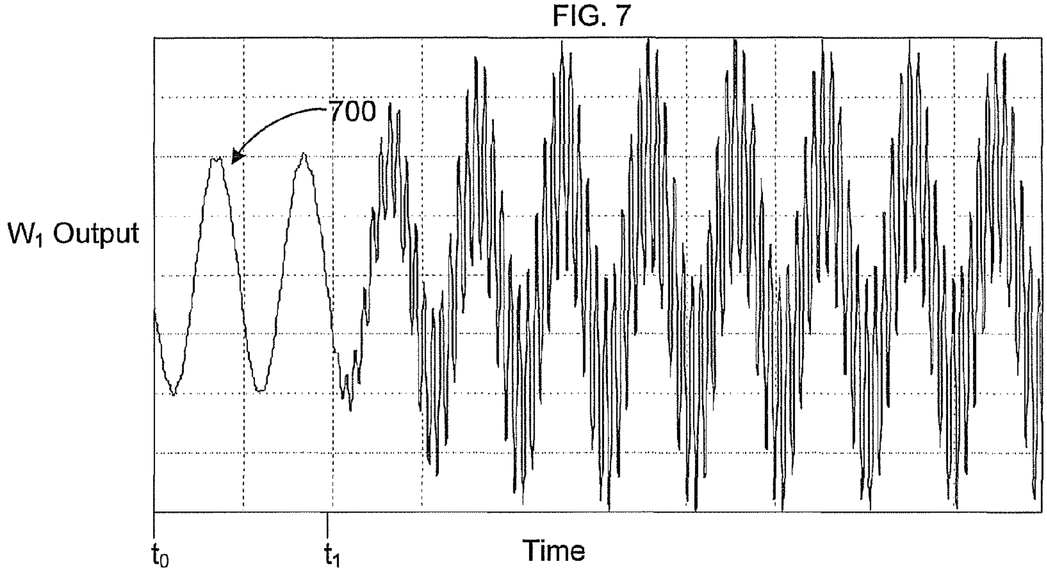
FIG. 7 is a plot of an output of an adaptive filter over time.
Figure 8:
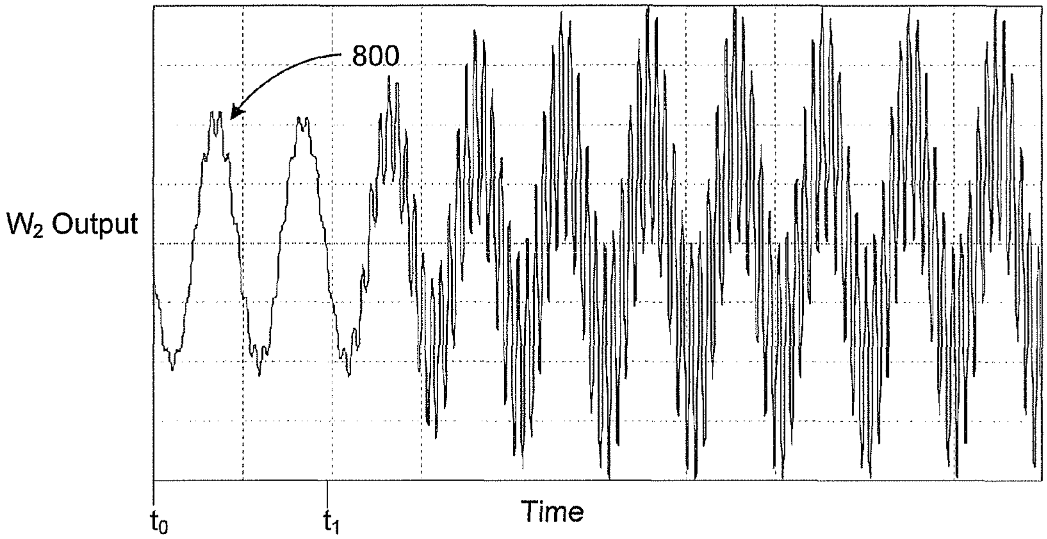
FIG. 8 is a plot of an output of another adaptive filter over time.
Figure 9:
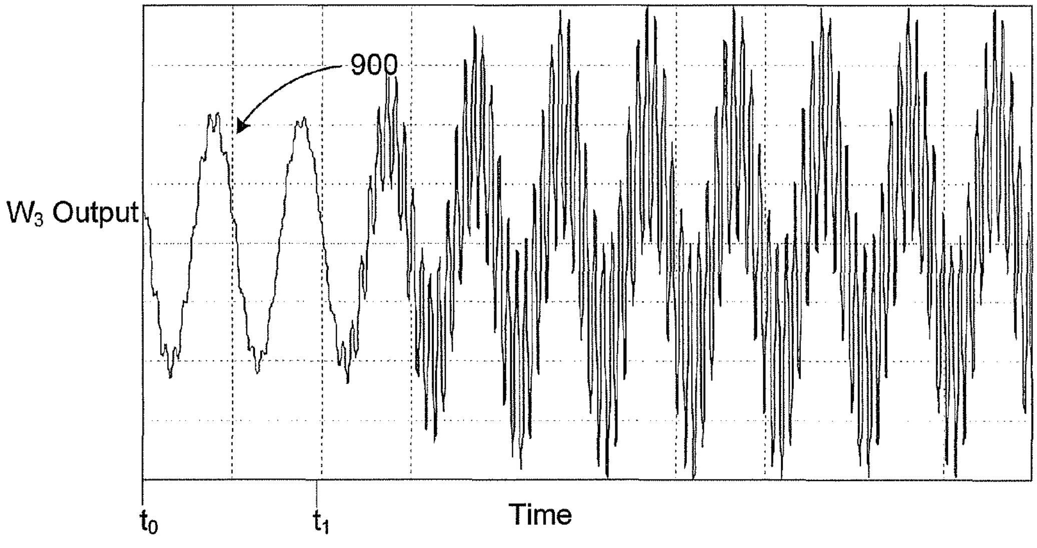
FIG. 9 is a plot of an output of another adaptive filter over time.

FIGS. 5 and 6 each show an ANC system producing anti-noise based on a 20 Hz reference signal. At time $t_0$, the reference signal is adjusted to 200 Hz. Time $t_1$ represents the moment in time that the error microphone detects the change in reference signal from 20 Hz to 200 Hz. In comparison of the error signals 500 and 600, the error signal 600 in FIG. 6 reduces to approximately zero by time $t_2$, while the error signal 500 in FIG. 5 is substantially present at time $t_2$. Thus, the three filter arrangement shows faster convergence as a whole. FIGS. 7-9 show the individual output of each filter operation of during and after 20 Hz to 200 Hz reference signal increase.

FIGS. 7-9 show individual performance of $W_1$, $W_2$, and $W_3$, respectively. Each filter $W_1$, $W_2$, and $W_3$ is of a different filter length relative to one another. The filter $W_1$ has the shortest length, followed by the filter $W_2$ with the filter $W_3$ being the longest. As shown in FIGS. 7-9, as the frequency increases from 20 Hz to 200 Hz, each filter output ultimately arrives at a steady state output, which indicates that each filter $W_1$, $W_2$, and $W_3$ is receiving an error signal of approximately zero. As shown in FIGS. 7-9, the shortest filter $W_1$ converges more quickly as illustrated by output waveform 700 at the time between $t_0$ and $t_1$. As compared to the other output waveforms, waveform 800 for the filter $W_2$ and waveform 900 for the filter $W_3$, the waveform 700 is smoother that waveforms 800 and 900 indicating that the filter $W_1$ is converging more quickly than the filters $W_2$ and $W_3$. Because the filter $W_1$ is shortest in filter length, the filter $W_1$ converges more quickly when a filter input signal includes a dominant component that increases in frequency as compared to the filters $W_2$ and $W_3$.

Figure 10:
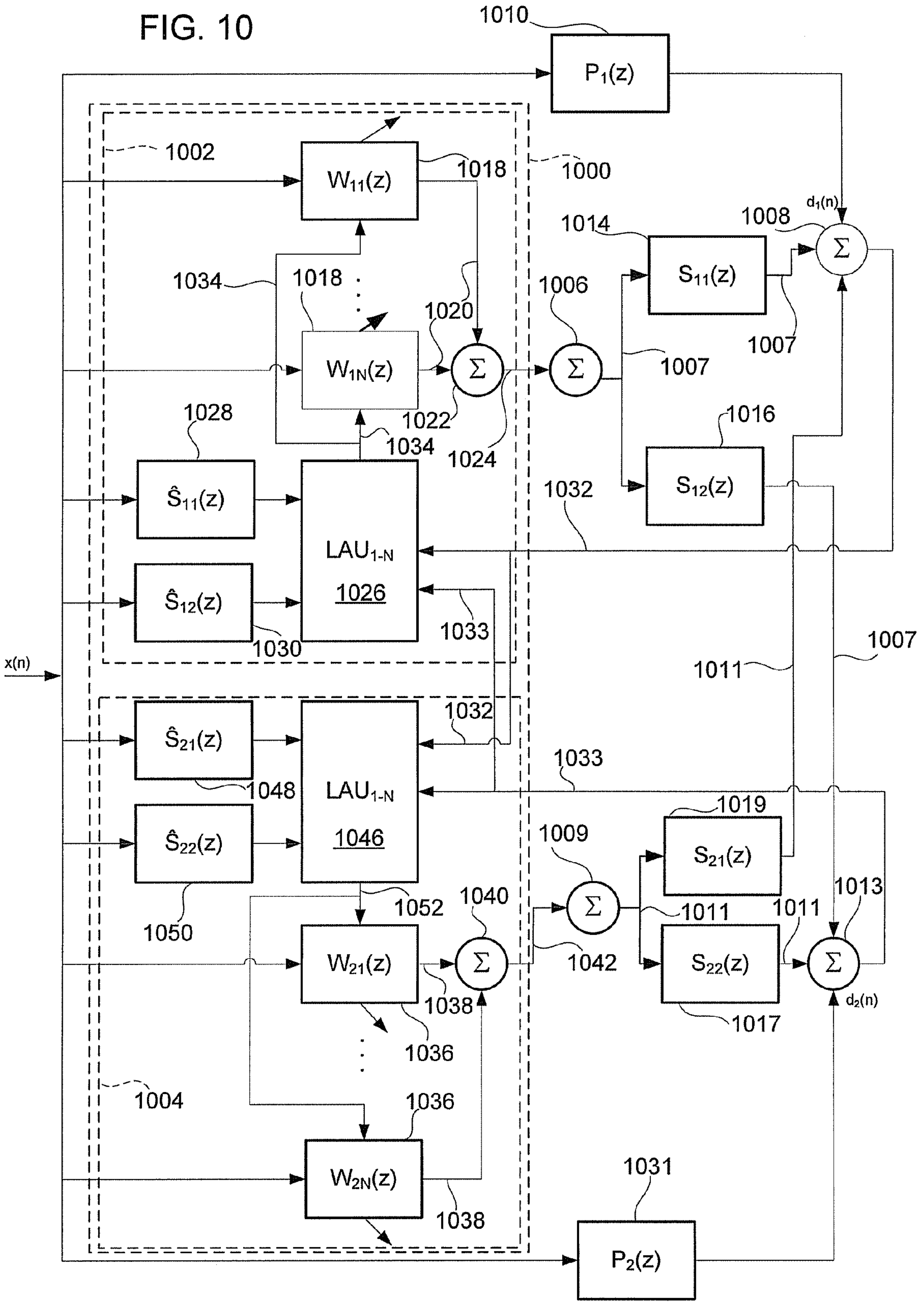
FIG. 10 is an example of a multi-channel ANC system.

FIG. 10 shows an example of a multi-channel ANC system 1000 in block diagram format. The ANC system 1000 may be implemented to generate anti-noise to destructively interfere with an undesired sound x(n) in a selected target space. In FIG. 10, the undesired sound is designated by a digital domain representation x(n). However, x(n) may represent both the analog and digitized versions of the undesired sound.

The ANC system 1000 may include a first channel 1002 and a second channel 1004. The first channel 1002 may be used to generate an anti-noise signal to drive a speaker 1006 (represented as a summation operation) to produce sound waves as speaker output 1007 to destructively interfere with the undesired sound present in a target space proximate to microphones 1008 and 1013, represented by a summation operation in FIG. 10. The second channel 1004 may be used to generate an anti-noise signal to drive a speaker 1009 (represented as a summation operation) to produce sound waves as speaker output 1011 to destructively interfere with the undesired sound present in a target space proximate to a microphones 1008 and 1013.

The undesired sound x(n) may traverse a physical path 1010 from a source to the microphone 1008 represented by $d_1(n)$. The physical path 1010 is designated as Z-domain transfer function $P_1(z)$ in FIG. 10. Similarly, the undesired sound x(n) may traverse a physical path 1031 from a source to the microphone 1013 designated as $d_2(n)$. The physical path 1031 may be designated as Z-domain transfer function $P_2(z)$ in FIG. 10. Sound waves produced as the speaker output 1007 may traverse the physical path 1014 from the speaker 1006 to the microphone 1008. The physical path 1014 is represented by Z-domain transfer function $S_{11}(z)$ in FIG. 10. The speaker output 1007 may also traverse a physical path 1016 from the speaker 1006 to the microphone 1013. The physical path 1016 is represented by Z-domain transfer function $S_{12}(z)$ in FIG. 10. Similarly, sound waves produced as the speaker output 1011 may traverse the physical path 1017 from the speaker 1009 to the microphone 1013. The physical path 1017 is represented by Z-domain transfer function $S_{22}(z)$ in FIG. 10. The speaker output 1007 may also traverse a physical path 1019 from the speaker 1009 to the microphone 1008. The physical path 1016 is represented by Z-domain transfer function $S_{21}(z)$ in FIG. 10.

The first channel 1002 may include a plurality of adaptive filters 1018, which are individually designated as $W_{11}(z)$-$W_{1N}(z)$. The adaptive filters 1018 may each have different filter lengths as discussed in regard to FIGS. 1-5. The adaptive filters 1018 may be configured to generate an output signal 1020 based on the undesired noise x(n). Each output signal 1020 may be summed at summation operation 1022. The output 1024 of the summation operation 1022 may be the anti-noise signal used to drive the speaker 1006. The adaptive filters 1018 receive an input signal of the undesired sound x(n), as well as an update signal from LAU 1026. The LAU 1026 shown in FIG. 10 may represent a plurality of LAU's 1-N, with each LAU 1026 corresponding to one of the adaptive filters 1018.

LAU 1026 may receive the undesired sound filtered by estimated path filters 1028 and 1030. The estimated path filter 1028 designated by Z-domain transfer function $\hat{S}_{11}(z)$ in FIG. 7 represents the estimated effect on sound waves traversing the physical path 1014. Similarly, the estimated path 1030 designated by Z-domain transfer $\hat{S}_{12}(z)$ in FIG. 10 represents the estimated effect on sound waves traversing the physical path 1016. Each LAU 1026 may also receive an error signal 1032 representative of the sound waves detected by the microphone 1008 and an error signal 1033 representative of sound waves detected by the microphone 1013. Each LAU 1026 may generate a respective update signal 1034, which may be transmitted to the corresponding adaptive filter 1018 similar to that discussed in regard to FIGS. 2 and 3.

Similarly, the second channel 1004 may include a plurality of adaptive filters 1036 designated individually as Z-domain transfer functions $W_{21}(z)$-$W_{2N}(z)$. Each adaptive filter 1036 may have a different filter length similar to that discussed in regard to FIGS. 1-5. Each adaptive filter 1036 may receive the undesired sound as an input signal to generate an output signal 1038. The output signals 1038 may be summed together at summation operation 1040. An output signal 1042 of the summation operation 1040 may be an anti-noise signal to drive the speaker 1009.

Similar to the first channel 1002, the second channel may include LAUs 1046. LAUs 1046 may receive the undesired noise filtered by estimated path filters 1048 and 1050. The estimated path filter 1048 represents the estimated effect on sound waves traversing the physical path 1019. The estimated path filter 1048 is designated as z-transform transfer function $\hat{S}_{21}(z)$ in FIG. 10. The estimated path filter 1050 represents the estimated effect on sound waves traversing the physical path 1017. The estimated path filter 1050 is represented by Z-domain transfer function $\hat{S}_{22}(z)$ in FIG. 10.

Each LAU 1046 may also each receive the error signals 1032 and 1033 to generate an update signal 1052. Each adaptive filter 1036 may receive a corresponding update signal 1052 to adjust its output signal 1038.

In other examples, the ANC system 1000 may implement more than two channels, such as 5, 6, or 7 channels, or any other suitable number. The ANC system 1000 may also be implemented on a compute device such as the computer device 302 shown in FIG. 3.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. An active noise control system comprising:

a computer device, a plurality of adaptive filters included in the computer device, each of the adaptive filters configured to receive an identical first input signal representative of an undesired sound and to receive a respective update signal that is different for each respective adaptive filter, where each of the adaptive filters are configured with a respective different filter length so that corresponding frequency ranges of the respective adaptive filters are different but overlapping, the respective different filter lengths of the adaptive filters configured to converge at different rates and generate respective output signals based on a frequency range of the first input signal, and a plurality of learning algorithm units included in the computer device and configured to all commonly and directly receive an identical error signal and an identical second input signal, and independently generate respective update signals for each of the respective adaptive filters using said identical error signal, where each of the respective output signals is independently adjusted by the respective adaptive filters based on the respective update signal received from a corresponding one of the learning algorithm units, and where the respective output signals are summed to form an anti-noise signal configured to drive a speaker to produce sound waves to destructively interfere with the undesired sound.

2. The active noise control system of claim 1, where the plurality of adaptive filters includes a first adaptive filter corresponding to a first predetermined frequency range and a second adaptive filter corresponding to a second predetermined frequency range, where the first adaptive filter is configured to converge at a faster rate than the second adaptive filter when the first input signal includes a dominant signal component within the first predetermined frequency range.

3. The active noise control system of claim 2, where the output signal of the first adaptive filter and the output signal of the second adaptive filter are summed together to produce the anti-noise signal, where the output signal of the first adaptive filter is a larger portion of the anti-noise signal than the output signal of the second adaptive filter when the dominant component of the first input signal is within the first predetermined frequency range.

4. The active noise control system of claim 2, where the output signal of the first adaptive filter and the output signal of the second adaptive filter are summed together to produce the anti-noise signal, where the output signal of the first adaptive filter is a smaller portion of the anti-noise signal than the output signal of the second adaptive filter when a dominant component of the first input signal is within the first predetermined frequency range.

5. The active noise control system of claim 2, where the second adaptive filter is configured to converge at a faster rate than the first adaptive filter when the first input signal includes a dominant component within the second predetermined frequency range.

6. The active noise control system of claim 2, where the first predetermined frequency range overlaps the second predetermined frequency range.

7. The active noise control system of claim 6, where each of the output signals is at least a portion of the anti-noise signal.

8. The active noise control system of claim 1, where the first input signal and the second input signal are different.

9. An active noise control system comprising:

a processor; and an active noise control system stored in memory and executable on the processor, where the active noise control system includes a plurality of adaptive filters and a plurality of learning algorithm units, where each of the adaptive filters is configured to receive an identical first input signal representative of undesired sound, and have a different filter length that corresponds to a different predetermined frequency range, each of the learning algorithm units corresponding to one of the adaptive filters, where all of the plurality of learning algorithm units are configured to independently generate a respective control signal for a respective one of the plurality of adaptive filters based on direct receipt of a second identical input signal representative of an undesired sound and an identical error signal indicative of audible sound in a target space; and where each of the plurality of adaptive filters are configured to:

receive an input signal representative of the undesired sound; and converge at different rates to generate a respective output signal based on a frequency range of the input signal, where the respective output signal of each of the plurality of adaptive filters is independently adjusted based on the respective control signal, and where at least one respective output signal is an anti-noise signal configured to drive a speaker to produce sound waves to destructively interfere with the undesired sound in the target space.

10. The active noise control system of claim 9, where the at least one respective output signal is generated by at least one of the plurality of adaptive filters that is first to converge.

11. The active noise control system of claim 9, where the plurality of adaptive filters includes a first adaptive filter having a first filter length and a second adaptive filter having a second filter length that is different from the first filter length.

12. The active noise control system of claim 11, where the first filter length corresponds to a first predetermined frequency range and the second filter length corresponds to a second predetermined frequency range, and where the first frequency range and the second frequency range overlap.

13. The active noise control system of claim 11, where the first filter length corresponds to a first predetermined frequency range and the second filter length corresponds to a second predetermined frequency range, and where the first adaptive filter is configured to converge faster than the second adaptive filter when the input signal includes a dominant signal component in the first predetermined frequency range.

14. The active noise control system of claim 9, where the plurality of adaptive filters are each configured to receive an entirety of the frequency range of the input signal.

15. The active noise control system of claim 9, where at least one of the adaptive filters is operable in a frequency range that is closest to the undesired sound is first to converge and to produce anti-noise configured to drive a speaker to produce sound waves to destructively interfere with the undesired sound.

16. The active noise control system of claim 9, where each adaptive filter is operable in a respective predetermined frequency range to converge to an anti-noise signal corresponding to an undesired sound in the respective predetermined frequency range.

17. The active noise control system of claim 9, where the input signal is a single input signal of a predetermined frequency range.

18. The active noise control system of claim 9, where the first input signal received by the adaptive filters is filtered with an estimated path filter to generate the second input signal received by the learning algorithm units.

19. A method of generating an anti-noise signal comprising:

receiving an input signal indicative of an undesired noise;

providing the input signal as a first identical input signal to each of a plurality of adaptive filters, and a second identical input signal to each of a plurality of learning algorithm units, where each of the plurality of adaptive filters has a different respective filter length corresponding to a respective different frequency range, different frequency ranges overlapping among different adaptive filters;

receiving at each of the plurality of learning algorithm units an identical error signal indicative of audible sound in a target space;

each learning algorithm unit independently generating a respective update signal for a respective one of the adaptive filters based on the second identical input signal and the identical error signal;

independently converging each of the plurality of adaptive filters as a function of frequencies in the first identical input signal at which dominant signal components are present, and generating an output signal from each of the plurality of adaptive filters based on the respective update signal;

summing the output signals from each of the plurality of adaptive filters; and generating the anti-noise signal based on the summed output signals.

20. The method of claim 19, where generating the anti-noise signal comprises generating the anti-noise signal based an at least one of the output signals from at least one of the plurality of adaptive filters that is first to converge.

21. The method of claim 19, where providing the first identical input signal to an input of each of a plurality of adaptive filters comprises providing the first identical input signal to a first input of a first adaptive filter corresponding to a first predetermined frequency range and a second input of a second adaptive filter corresponding to a second predetermined frequency range, where the first adaptive filter converges faster than the second adaptive filter when the first identical input signal includes a dominant signal component in the first frequency range.

22. The method of claim 19, where the first identical input signal is provided directly and in parallel to the plurality of adaptive filters, and the second identical input signal is provided directly and in parallel to the plurality of learning algorithm units.

23. The method of claim 19, further comprising filtering the first identical input signal with an estimated path filter to generate the second identical input signal.

24. A non-transitory computer-readable medium encoded with computer executable instructions, the computer executable instructions executable with a processor, the computer-readable medium comprising:

instructions executable to receive an input signal representative of an undesired sound;

instructions executable to generate a plurality of adaptive filters;

instructions executable to provide the input signal directly and in parallel as an identical first input signal to all of the plurality of adaptive filters, where each of the plurality of adaptive filters has a different respective filter length corresponding to a respective different frequency range, and different frequency ranges of different respective adaptive filters are overlapping;

instructions executable to generate a respective control signal for each of the plurality of adaptive filters, each of the respective control signals independently generated based on an identical second input signal and receipt of an identical error signal indicative of audible sound in a target space;

instructions executable to independently converge each of the plurality of adaptive filters as a function of frequencies in the input signal at which dominant signal components are present, and generate a plurality of output signals, where each of the plurality of output signals corresponds to an output of one of the plurality of adaptive filters, and each of the plurality of output signals is independently generated based on a respective one of the control signals;

instructions executable to sum the plurality of output signals; and instructions executable to generate an anti-noise signal based on the summed plurality of output signals, where the anti-noise signal is configured to drive a speaker to produce sound waves to destructively interfere with the undesired sound.

25. The non-transitory computer-readable medium of claim 24 further comprising instructions executable to generate an anti-noise signal based on a first one of the plurality of output signals corresponding to a first one of the plurality of adaptive filters that converges.

26. The non-transitory computer-readable medium of claim 24 further comprising:

instructions executable to generate a first adaptive filter having a first filter length and a second adaptive filter having a second filter length that is different from the first filter length; and instructions executable to transmit the identical first input signal to an input of each of a first input of the first adaptive filter and a second input of the second adaptive filter.

27. The non-transitory computer readable medium of claim 26, where the first filter length corresponds to a first predetermined frequency range and the second filter length corresponds to a second predetermined frequency range, where the first predetermined frequency range and the second predetermined frequency range overlap.

28. The non-transitory computer readable medium of claim 24 further comprising:

instruction executable to generate a first input of a first adaptive filter corresponding to a first predetermined frequency range and a second input of a second adaptive filter corresponding to a second predetermined frequency range; and instructions executable to transmit the first input signal to a first input of the first adaptive filter and to a second input of the second adaptive filter, where the first adaptive filter converges faster than the second adaptive filter when the input signal includes a dominant signal component in the first frequency range.

* * * * *